United States Patent [19]

Ishimaru

[11] 4,064,122
[45] Dec. 20, 1977

[54] HYDROXY-SUBSTITUTED CEPHALOSPORINS

[76] Inventor: Toshiyasu Ishimaru, D-14, 2-7, Momoyamadai, Suita, Japan

[21] Appl. No.: 607,361

[22] Filed: Aug. 25, 1975

[30] Foreign Application Priority Data

Aug. 26, 1974   Japan .................................. 48-98045

[51] Int. Cl.$^2$ ................. C07D 501/36; C07D 501/20; A61K 31/545
[52] U.S. Cl. .................................... 544/26; 424/246; 544/24; 544/30; 544/16
[58] Field of Search .................................... 260/243 C

[56] References Cited

U.S. PATENT DOCUMENTS 3,855,213   12/1974   Dunn et al. ..................... 260/243 C

FOREIGN PATENT DOCUMENTS 1,082,943   9/1967   United Kingdom.

*Primary Examiner*—Nicholas S. Rizzo
*Attorney, Agent, or Firm*—Hubbell, Cohen, Stiefel & Gross

[57] ABSTRACT

Hydroxy-substituted cephalosporins, particularly 7-(α-hydroxy-arylacetamido)-3-substituted-3-cephem-4-carboxylic acids of the formula:

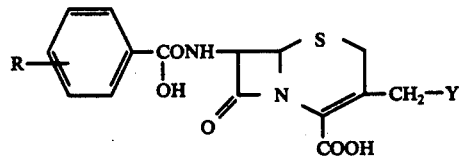

wherein R is a hydrogen atom, an esterified carboxy or carboxy group, and Y is a lower alkanoyl, lower alkoxy or azido group or a group of the formula: —SR$_3$ in which R$_3$ is a heterocyclic residue. These compounds have antibacterial activity against Gram-positive and Gram-negative bacteria.

8 Claims, No Drawings

HYDROXY-SUBSTITUTED CEPHALOSPORINS

The present invention is concerned with hydroxy-substituted cephalosporins and the preparation thereof.

According to the invention, there are provided 7-(α-hydroxy-arylacetamido)-3-substituted-3-cephem-4-carboxylic acids of the formula:

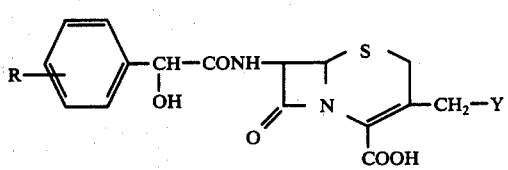

(I)

wherein R is a hydrogen atom, an esterified carboxy or carboxy group, and Y is a lower alkanoyl, lower alkoxy or azido group or a group of the formula: —SR₃ in which R₃ is a heterocyclic residue, and pharmaceutically acceptable non-toxic salts thereof.

Among the compounds (I) of the present invention, 7-(α-hydroxy-phenylacetamido)-3-(1-methyl-1H-1,2,3,4-tetrazol-5-yl)thiomethyl-3-cephem-4-carboxylic acid is a known compound, the 7-acyl group of which has been introduced by the use of anhydro-o-carboxymandelic acid prepared from mandelic acid and phosgene(e.g., Japanese Patent Laying Open No. 5987/1974).

It is an object of the invention to provide a series of new compounds which are of value as antibacterial antibiotics having potent activity against Gram-positive and Gram-negative bacteria.

It is another object of the invention to provide a new method for preparing these new compounds as well as the known compound in good yields, without using dangerous reagents such as phosgene. Still another object of the invention is to provide a new method using acylating agents which can be conveniently manufactured and in which a protecting group for the hydroxy group can be easily removed after acylation.

Other objects and features of the invention will become apparent from the following description.

A class of new compounds according to the invention may be represented by the following general formula:

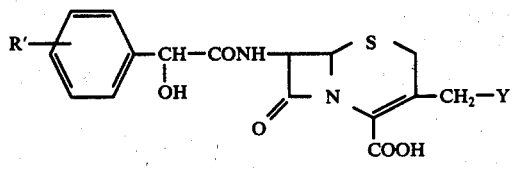

(II)

wherein R' is an esterifed carboxy or carboxy group and Y is as defined above. The α-carbon atom of the acyl group to which the α-hydroxy group is attached, is an asymmetric carbon atom and the compounds of the present invention can therefore exist in two optically active isomeric forms, as well as in the optically inactive form which is a mixture of the two optically active forms. All such isomeric forms of the compound (II) are included in the scope of the invention.

The compounds (I) of the invention may be prepared by reacting a 7-aminocephalosporanic acid derivative having the general formula:

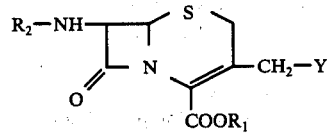

(III)

wherein Y is as defined above, and $R_1$ and $R_2$, which may be the same or different, are hydrogen atoms or radicals which may be easily removed by hydrolysis, with a reactive derivative of an α-haloacyloxy-arylacetic acid having the general formula:

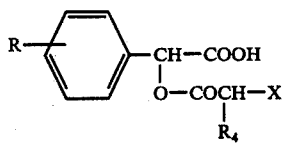

(IV)

wherein R is as defined above, X is a halogen atom and R4 is a hydrogen atom or a lower alkyl group, and treating the resulting 7-(α-haloacyloxy-arylacetylated)-aminocephalosporanic acid derivative with thiourea or an N-mono or di-substituent thereof, and if desired, de-esterifying the compound of R' being esterified carboxy group.

In the 7-aminocephalosporanic acid derivatives (III) as the starting materials, the term "a radical which may be easily removed by hydrolysis" in the symbols $R_1$ and $R_2$ means a radical which is formed by the 4-carboxy group of the compound (III) in which both of $R_1$ and $R_2$ are hydrogen atoms, and a phosphorus compound, such as 2-chloro-1,3,2-dioxaphospholane, 2-chloro-4-methyl-1,3,2-dioxaphospholane, methoxyphosphonyl dichloride, methylphosphonyl dichloride or the like, or a silyl compound, such as trimethylchlorosilane, dimethyldichlorosilane, methyldimethoxychlorosilane, methoxy-methyldichlorosilane, dimethoxydichlorosilane, hexamethyldisilanzane, N,O-bis-trimethylsilyltrifluoroacetamide, N,O-bis-trimethylsilyl-acetamide or the like. The preferred compounds are trimethylchlorosilane, trimethoxychlorosilane, hexamethyldisilazane, 2-chloro-1,3,2-dioxaphospholane or the like. Moreover, $R_1$ may be a cation of an alkali metal, ammonium, trialkylammonium, N-methylpiperadinum, N-methylmorpholinum or the like. These radicals which may be easily removed by hydrolysis are selected, taking into due consideration the nature of the desired compounds (I), the acylation conditions and the like.

The heterocyclic residue $R_3$ includes those derived from heterocyclic thiol compounds containing at least a nitrogen, sulfur or oxygen atom. As preferred examples of $R_3$—SH as the raw material may be mentioned:
1,3,4-thiadiazol-2-thiol,
5-methyl-1,3,4-thiadiazol-2-thiol,
1,3,4-triazol-2-thiol,
1-methyl-1,3,4-triazol-2-thiol,
1,5-dimethyl-1,3,4-triazol-2-thiol,
1,3,4-oxadiazol-2-thiol,
5-methyl-1,3,4-oxadiazol-2-thiol,
1H-1,2,3,4-tetrazol-5-thiol,
1-methyl-1H-1,2,3,4-tetrazol-5-thiol,
1-oxopyridin-2-thiol and like.
Besides, there are 1-methylimidazol-2-thiol, pyrimidine-2-thiol and the like.

In the method of the present invention, the α-haloacyloxyaryl acetic acids (IV) used as the acylating agent are usually converted into their reactive derivatives and then they are allowed to react with 7-aminocephalosporanic acid derivatives (III). When a condensing agent is used for the acylation, it is considered that almost all of the α-haloacyloxy-arylacetic acids (IV) are converted into their reactive derivatives, which react with 7-aminocephalosporanic acid derivatives (III). Therefore, an explanation of the reactive derivatives of the compounds (IV) to be formed will be given below, omitting explanation of the condensing agents.

Thus, as the reactive derivatives of the α-haloacetoxyaryl acetic acids there may be mentioned the acid halides such as the acid chloride or acid bromide; the mixed anhydrides with acid derivatives such as i-butylyl halide, trimethylacetyl halide (pivaloyl chloride), methyl chloroformate, ethyl chloroformate, i-propyl chloroformate, i-butyl chloroformate, phosphoric acid alkyl ester or phosphorus oxychloride; the active ester-type intermediates with dicyclohexylcarbodiimide, hexamethylcarbodiimide, keteninime or isooxazolium salt; the active esters such as the p-nitrophenyl ester, propargyl ester, carboxymethylthio ester, N-hydroxysuccinimide ester or cyanomethyl ester, and the like. The reactive derivatives are not particularly limited and can be selected from those which are known in the field of peptide synthesis. Of course, the active ester may be used in the presence of an acidic or basic accelerator. A preferred example, from an industrial viewpoint, is the mixed anhydride with alkyl chloro.

As the α-haloacyloxy-arylacetic acids (IV) used there may be mentioned α-chloroacetoxyphenylacetic acid, α-chloroacetoxy-m or p-(p-methoxybenzyloxycarbonyl)phenylacetic acid, α-chloro-acetoxy-m- or p-(p-nitrobenzyloxycarbonyl)phenylacetic acid, α-chloroacetoxy-m or p-(2,2,2-trichloroethoxycarbonyl)-phenylacetic acid, α-chloroacetoxy-m or p-(phenacyloxycarbonyl)phenylacetic acid, α-chloroacetoxy-m or p-(diacetylmethoxycarbonyl) phenylacetic acid, α-chloroacetoxy-m or p-(1-methoxy-(or ethoxy) carbonyl-2-oxopropan-1-yl-oxycarbonyl)-phenylacetic acid and the like, as well as their corresponding α-bromoacetoxy, α-chlorobutylyloxy compounds.

The acylation may usually be conducted in an aqueous solution, a methanol solution or an aqueous organic solvent solution, containing an alkali metal salt or tertiary amine (e.g., triethylamine)salt of a 7-aminocephalosporanic acid derivative (III). On the other hand, when the compound (III) with $R_1$ and/or $R_2$ being radicals formed with the silyl or phosphorus compound is used, the reaction is usually conducted in an anhydrous inert organic solvent.

Among the organic solvents used herein there are included acetone, acetonitrile, isobutyl methyl ketone, methylene chloride, ethylene chloride, chloroform, carbon tetrachloride, trichloroethane trichloroethylene, 1,2-dichloropropane, dimethylformamide, dioxane, tetrahydrofuran, ethylene glycol dimethylether and the like.

The acylation may be carried out at $-50° \sim +30°$ C, preferably at $-30° \sim +10°$ C. A reaction time of one to four hours at $-20° \sim 0°$ C, although it depends upon the kind of reactive derivatives of the acylating agents (IV), the compounds (III) and the solvents.

Next, the protecting group (i.e., haloacyl group) in the resultant product is removed. This may be achieved by treating the resultant with thiourea or an N-mono or di-substituent thereof, usually in an aqueous solution. The N-mono or disubstituted thioureas to be used are N-methylthiourea, N-phenylthiourea, N-benzylthiourea, N-cyclohexylthiourea, N,N'-dimethylthiourea N,N'-diphenylthiourea, N,N'-dicyclohexylthiourea and the like. These materials are desirably selected from those which are available or can be manufactured at low cost.

The removal is carried out usually at a pH of $5 \sim 8$ preferably at a pH of $5.5 \sim 7$. As the pH value varies during the reaction, it is recommended to adjust some with the addition of an alkali. Especially, the use of a buffer such as a phosphate or borate buffer is convenient. A conventional solvent in this reaction is water, to which may be added a water-soluble organic solvent such as acetone, methanol, tetrahydrofuran or acetonitrile. The reaction will be complete, e.g., for 3 to 16 hours at pH 6.8 and at $50° \sim 60°$ C, although the time depends upon the reaction temperatures. The reaction can be monitored by thin-layer chromatography.

Besides, when the acylated product in which $R_1$ and/or $R_2$ are radicals which may be easily removed by hydrolysis is used, such radicals will be very conveniently hydrolyzed during the removal of the protecting group, by which the compound (I) wherein $R_1$ and $R_2$ are hydrogen atoms is produced.

After completing the above reactions, the reaction mixture is treated in accordance with conventional procedures, e.g., it is distilled in vacuo to remove the solvent, subjected to treatment with active carbon and treatment for removal of water-insoluble by-products and then extracted at a pH of $2 \sim 3$ to recover the desired compound.

If desired, a compound (I) which has an esterified carboxy group, such as a methoxybenzyloxy or tert.-butoxy-carbonyl group, can be converted into a compound having a free carboxy group by reductive decomposition, using zinc and a mineral or organic acid, or by treatment with trifluoroacetic acid.

Interesting new compounds according to the invention include:
1. 7-(α-hydroxy-4(or 3)-carboxyphenylacetamido)-3-(5-methyl-1,3,4-thiadiazol-2-yl)thiomethyl-3-cephem-4-carboxylic acid,
2. 7-(α-hydroxy-4(or 3)-carboxyphenylacetamido)-3-(1,3,4-thiadiazol-3-cephem-4-carboxylic acid,
3. 7-(α-hydroxy-4(or 3)-carboxyphenylacetamido)-3-azidomethyl-3-cephem-4-carboxylic acid,
4. 7-(α-hydroxy-4(or 3)-carboxyphenylacetamido)-3-(1-methyl-1H-1,2,3,4-tetrazol-5-yl)thiomethyl-3-cephem-4-carboxylic acid,
5. 7-(α-hydroxy-4(or 3)-carboxyphenylacetamido)cephalosporanic acid,
6. 7-(α-hydroxy-4(or 3)-carboxyphenylacetamido)-3-(5-methyl-1,3,4-triazol-2-yl)thiomethyl-3-cephem-4-carboxylic acid,
7. 7-(α-hydroxy-4(or 3)-carboxyphenylacetamido)-3-(1,3,4-triazol-2-yl)thiomethyl-3-cephem-4-carboxylic acid,
8. 7-[α-hydroxy-4(or 3)-(p-methoxybenzyloxycarbonyl)phenylacetamido]-3-(5-methyl-1,3,4-thiadiazol-2-yl)thiomethyl-3-cephem-4-carboxylic acid, 9. 7-[α-hydroxy-4(or 3)-(p-methoxybenzyloxycarbonyl)phenylacetamido]-3-(1,3,4-thiadiazol-2-yl)thiomethyl-3-cephem-4-carboxylic acid,
10. 7-[α-hydroxy-4(or 3)-(p-methoxybenzyloxycarbonyl)phenylacetamido]-3-azidomethyl-3-cephem-4-carboxylic acid,
11. 7-[α-hydroxy-4(or 3)-(p-methoxybenzyloxycarbonyl)phenylacetamido]-3-(1-methyl-1H-1,2,3,4-tetrazol-5-yl)thiomethyl-3-cephem-4-carboxylic acid,
12. 7-[α-hydroxy-4(or 3)-(p-methoxybenzyloxycarbonyl)phenylacetamido]cephalosporanic acid,
13. 7-[α-hydroxy-4(or 3)-(p-methoxybenzyloxycarbonyl)phenylacetamido]-3-(5-methyl-1,3,4-triazol-2-yl)thiomethyl-3-cephem-4-carboxylic acid,
14. 7-[α-hydroxy-4(or 3)-(p-methoxybenzyloxycarbonyl)phenylacetamido]-3-(1,3,4-triazol-2-yl)thiomethyl-3-cephem-4-carboxylic acid,
15. 7-(α-hydroxy-4(or 3)-ethoxycarbonylphenylacetamido)-3-(5-methyl-1,3,4-thiadiazol-2-yl)thiomethyl-3-cephem-4-carboxylic acid,
16. 7-(α-hydroxy-4(or 3)-ethoxycarbonylphenylacetamido)-3-(1,3,4-thiadiazol-2-yl)thiomethyl-3-cephem-4-carboxylic acid,
17. 7-(α-hydroxy-4(or 3)-ethoxycarbonylphenylacetamido)-3-azido-methyl-3-cephem-4-carboxylic acid,
18. 7-(α-hydroxy-4(or 3)-ethoxycarbonylphenylacetamido)-3-(1-methyl-1H-1,2,3,4-tetrazol-5-yl)thiomethyl-3-cephem-4-carboxylic acid,
19. 7-(α-hydroxy-4(or 3)-ethoxycarbonylphenylacetamido)cephalosporanic acid,
20. 7-(α-hydroxy-4(or 3)-ethoxycarbonylphenylacetamido)-3-(5-methyl-1,3,4-triazol-2-yl)thiomethyl-3-cephem-4-carboxylic acid,
21. 7-(α-hydroxy-4(or 3)-ethoxycarbonylphenylacetamido)-3-(1,3,4-triazol-2-yl)thiomethyl-3-cephem-4-carboxylic acid,
22. 7[α-hydroxy-4(or 3)-(2-methylpropoxycarbonyl)phenylacetamido]-3-(5-methyl-1,3,4-thiadiazol-2-yl)thiomethyl-3-cephem-4-carboxylic acid,
23. 7-[α-hydroxy-4(or 3)-(2-methylpropoxycarbonyl)phenylacetamido]-3-(1,3,4-thiadiazol-2-yl)thiomethyl-3-cephem-4-carboxylic acid,
24. 7-[α-hydroxy-4(or 3) -(2-methylpropoxycarbonyl)phenylacetamido]-3azidomethyl-3-cephem-4-carboxylic acid,
25. 7-[α-hydroxy-4(or 3)-(2-methylpropoxycarbonyl)phenylacetamido]-3-(1-methyl-1H-1,2,3,4-tetrazol-5-yl)thiomethyl-3-cephem-4-carboxylic acid,
26. 7-[α-hydroxy-4(or 3)-(2-methylpropoxycarbonyl)phenylacetamido]cephalosporanic acid,
27. 7-[α-hydroxy-4(or 3)-(2-methylpropoxycarbonyl)phenylacetamido]-3-(5-methyl-1,3,4-triazol-2-yl)thiomethyl-3-cephem-4-carboxylic acid,
28. 7-[α-hydroxy-4(or 3)-(2-methylpropoxycarbonyl)phenylacetamido]-3-(1,3,4-triazol-2-yl)thiomethyl-3-cephem-4-carboxylic acid,
29. 7-[α-hydroxy-4(or 3)-(p-nitrobenzyloxycarbonyl)phenylacetamido]-3-(5-methyl-1,3,4-thiadiazol-2-yl)thiomethyl-3-cephem-4-carboxylic acid,
30. 7-[α-hydroxy-4(or 3)-(p-nitrobenzyloxycarbonyl)phenyl-acetamido]-3-(1,3,4-thiadiazol-2-yl)thiomethyl-3-cephem-4-carboxylic acid,
31. 7-[α-hydroxy-4(or 3)-(p-nitrobenzyloxycarbonyl)phenylacetamido]-3-azidomethyl-3-cephem-4-carboxylic acid,
32. 7-[α-hydroxy-4(or 3)-(p-nitrobenzyloxycarbonyl)phenylacetamido]-3-(1-methyl-1H-1,2,3,4-tetrazol-5-yl)thiomethyl-3-cephem-4-carboxylic acid,
33. 7-[-hydroxy-4(or 3)-(p-nitrobenzyloxycarbonyl)phenylacetamido]cephalosporanic acid,
34. 7-[α-hydroxy-4(or 3)-(p-nitrobenzyloxycarbonyl)phenylacetamido]-3-(5-methyl-1,3,4-triazol-2-yl)thiomethyl-3-cephem-4-carboxylic acid,
35. 7-[α-hydroxy-4(or 3)-(p-nitrobenzyloxycarbonyl)phenylacetamido]-3-(1,3,4-triazol-2-yl)thiomethyl-3-cephem-4-carboxylic acid.

The thus obtained object compounds (I) may be converted into the corresponding pharmaceutically acceptable non-toxic salts in accordance with conventional procedures.

The pharmaceutically acceptable non-toxic salts include the metallic salts, such as sodium, potassium, calcium and aluminum salts, as well as amine, ammonium and substituted ammonium salts or basic amino acid salts such as arginine, lysine and ornithine salts, which are known in the art.

The compounds (I) of the invention possess potent activity against Gram-positive and Gram-negative bacteria and can be used as therapeutic agents. However, they, if needed, may be converted into other useful cephalosporins by subjecting to replacement of the 3-substituents and conversion of the 7-acryl groups.

The following Examples are given for the purpose of illustrating the present invention.

EXAMPLE 1 a. Preparation of D-α-Chloroacetoxyphenylacetic Acid

Chloroacetyl chloride, 3.73 g were added to 20 ml of a methylene chloride solution containing 4 ml of anhydrous pyridine at 0° C and stirred for 20 minutes. On the other hand, 4.5 g of D-mandelic acid were dissolved in 20 ml of methylene chloride and cooled to −20° C. To this solution was added the above mentioned pyridine solution. After stirring for an hour at 0° ∼ 10° C, 20 ml of ice-water were added to the reaction mixture, adjusted to pH 1.5 ∼ 2.0 with 20% hydrochloric acid and stirred for 30 minutes. The methylene chloride layer was separated and the aqueous layer was saturated with sodium chloride and extracted several times with methylene chloride. The combined organic layers were washed two times with a small amount of an aqueous saturated sodium chloride solution.

Then 10 ml of ice-water were added and the mixture was adjusted to pH 7.5 with 5% sodium hydrogen carbonate while stirring. The aqueous layer was adjusted to pH 1.5 ∼ 2.0 and extracted three times with methylene chloride.

The combined organic layers were washed 3 times with a small amount of an aqueous saturated sodium chloride solution, dried over anhydrous magnesium sulfate and distilled in vacuo to give a viscous liquid 6.15g (90%) of D-α-chloroacetoxyphenylacetic acid. IR (KBr) : 1758, 1730, 1160 $cm^{-1}$.

b. PREPARATION OF 7-(D-α-CHLOROACETOXY-PHENYLACETAMIDO)-3-(1-METHYL-1H-1,2,3,4-TETRAZOL-5-YL)THIOMETHYL-3-CEPHEM-4-CARBOXYLIC ACID:

0.15 g (2.2 m mol) of D-α-chloroacetoxyphenylacetic acid and 0.23 g (2.2 m mol) of N-methyl-morpholine were dissolved in 5 ml of anhydrous methylene chloride. To the solution were dropped 0.28 g (0.25 m mol) of ethyl chloroformate in 2 ml of methylene chloride at −30° C, while stirring. Stirring was continued for an hour at −20° ∼ −15° C and further for 30 mins. at −10° C, and cooled to −30° C. Then a solution of 0.66 g (2 m mol) of 7-amino-3-(1-methyl-1H-1,2,3,4-tetrazol-5-yl)thiomethyl-3-cephem-4-carboxylic acid and 0.56 ml of triethylamine in 12 ml of methanol was dropped into the above mentioned mixed anhydride solution over the course of 10 minutes with stirring. The reaction was continued for an hour at −15° ∼ −10° C, and further for 30 minutes at 0° C.

The solvent was removed in vacuo, and to the residue were added 15 ml of ethyl acetate and 15 ml of ice-water. After adjusting to pH 7.5 with 5% sodium hydrogen carbonate, the aqueous layer was separated. The organic layer was extracted with 10 ml of water. To the combined aqueous layers were added 15 ml of ethyl acetate, which then was adjusted to pH 3.4 with 20% hydrochloric acid. The mixture was filtered, to remove insoluble materials. The filtrate after adjusting to pH 2.0 with hydrochloric acid was saturated with sodium chloride. The organic layer was separated and the aqueous layer was extracted three times with ethyl acetate.

The combined organic layers were washed three times with a small amount of a saturated sodium chloride solution, and dried over anhydrous magnesium sulfate.

The solvent was removed in vacuo and the residue was treated with ethyl ether and n-hexane to give a fine powder of 7-(D-α-chloroacetoxyphenylacetamido)-3-(1-methyl-1H-1,2,3,4-tetrazol-5-yl)thiomethyl-3-cephem-4-carboxylic acid of 0.79 g (73%).

IR (KBr) : 1770 cm$^{-1}$ UV λmax : 273 n.m. (95% ethanol).

TLC :Rf = 0.60 (acetonitrile : water = 4:1, with iodoazide being used as a coloring agent).

c. Preparation of 7-(D-α-Hydroxy-Phenylacetamido)-3-(1-Methyl-1H-1,2,3,4-Tetrazol-5-yl)Thiomethyl-3-Cephem-4-Carboxylic Acid 0.54 g (1 m mol) of 7-(D-α-chloroacetoxyphenylacetamido)-3-(1-methyl-1H-1,2,3,4-tetrazol-5-yl)thiomethyl-3-cephem-4-carboxylic acid and 0.068 g (1.1 m mol) of thiourea were dissolved in 5 ml of acetone and 15 ml of a phosphate buffer solution (0.2 mol, pH 6.3). The solution was adjusted to pH 6.5 with a sodium hydrogen carbonate solution an heated at 45° C for 12 hours while stirring. Acetone was removed in vacuo and 15 ml of ethyl acetate were added to the residue.

The solution was adjusted to pH 9.0 with a sodium hydroxide solution under ice-cooling, and stirred for 5 minutes. The aqueous layer was separated and the organic layer was washed with water. The combined aqueous layers were added to 15 ml of ethylacetate, adjusted to pH 2.0 with phosphoric acid. The ethylacetate layer was separated, and the aqueous layer was extracted three times with 10 ml of ethyl acetate. The combined ethyl acetate layers were washed three times with a small amount of a saturated sodium chloride solution, dried over anhydrous magnesium sulfate and the solvent removed in vacuo. The residue was treated with ethyl ether and n-hexane to give a fine powder (0.40 g, 86%) of 7-(D-α-hydroxy-phenylacetamido)-3-(1-methyl-1H-1,2,3,4-tetrazol-5-yl)thiomethyl-3-cephem-4-carboxylic acid IR: 1770 cm$^{-1}$, UV λmax : 273 n.m. (95% ethanol).

EXAMPLE 2 a. Preparation of 7-(D-α-Chloroacetoxyphenylacetamido) Cephalosporanic Acid 0.25 g (1.1 m mol) of D-α-chloroacetoxyphenylacetic acid and 0.12 g (1.1 m mol) of N-methylmorpholine were dissolved in 3 ml of anhydrous methylene chloride. To this solution were added dropwise 0.14 g (1.2 m mol) of ethyl chloroformate in 2 ml of anhydrous methylene chloride over the course of 5 minutes at −30° C. Stirring was continued for an hour at −15° C and further for 30 minutes at −10° C and the mixture was cooled to −30° C. Further a solution of 0.27 g (1 m mol) of 7-aminocephalosporanic acid and 0.28 ml of triethylamine in 7 ml of methanol, were added dropwise to the above mixed anhydride solution with stirring over the course of 10 minutes. The mixture was stirred for an hour at −20° ∼ −10° C and further for 30 minutes. at 0° C. The solvent was removed in vacuo. 10 ml of ethyl acetate and 10 ml of ice-water were added to the residue, followed by adjustment to pH 7.5 with sodium hydrogen carbonate. The aqueous layer was separated and the organic layer was extracted with 10 ml of water.

The combined aqueous layers were adjusted to pH 3.5 with an aqueous citric acid saturated solution, to remove insoluble materials. Then the aqueous layer was adjusted to pH 2.5 with an aqueous citric acid solution and saturated with sodium chloride. The aqueous layer was extracted further three times with ethyl acetate. The combined organic layers were washed two times with a small amount of an aqueous sodium chloride saturated solution and dried over anhydrous magnesium sulfate. After evaporating the solvent in vacuo, the residue was treated with ethyl ether and n-hexane to give a fine powder (0.42 g (73%)) of 7-(D-α-chloroacetoxyphenylacetamido)-cephalosporanic acid.

b. Preparation of 7-(D-α-Hydroxyphenylacetamido)-Cephalosporanic acid 0.24 g (0.5 m mol) of 7-(D-α-chloroacetoxyphenylacetamido)-cephalospornaic acid and 0.043g (0.55 m mol) of thiourea were dissolved in 3 ml of acetone and 10 ml of a phosphate buffer solution (0.2 mol, pH 6.3), and adjusted to pH 6.5 with an aqueous sodium hydrogen carbonate solution. This mixture was stirred at 45° C for 12 hours. Then 10 ml of ethyl acetate were added to the reaction mixture, followed by adjustment to pH 9.0 with an aqueous sodium carbonate solution under ice-cooling. After stirring for 5 minutes there were added to the separated aqueous layer 10 ml of ethyl acetate, which was adjusted to pH 2.5 with an aqueous phosphoric acid solution. The mixture was saturated with sodium chloride and the ethyl acetate layer was separated. The aqueous layer was extracted three times with ethyl acetate. The combined organic layers were washed three times with a small amount of an aqueous saturated sodium chloride solution, dried over anhydrous magnesium sulfate. After evaporating the solvent in vacuo, the residue was treated with ether and n-hexane to give a fine powder (0.18 g (86%)) of 7-(D-α-hydroxyphenylacetamido)-cephalosporanic acid.

IR : 1770 cm$^{-1}$, UV λmax : 263 n.m. (95% ethanol).

EXAMPLE 3 a. Preparation of DL-α-Hydroxy-4-(P-Methoxybenzyloxycarbonyl)-Phenylacetic Acid To a suspension of 4.9 g of the dipotassium salt of DL-α-hydroxy-4-carboxyphenylacetic acid (mp 201° ~ 203° C) in 40 ml of dimethylsulfoxide were added 6.2 g p-methoxybenzylchloride and stirred overnight at ambient temperature. 50 ml of ice-water were added to the reaction mixture, adjusted to pH 7.5 and extracted several times with ethyl acetate. The combined ethyl acetate layers were washed with water, dried over anhydrous magnesium sulfate and evaporated in vacuo. The oily residue was dissolved in 60 ml of 50% acetone. To the solution was added a phenolphthalein reagent and then dropwise a 2N-sodium hydroxide solution at 40° ~ 45° C with stirring. The reaction was continued until the red color was maintained for 5 minutes. Then acetone was removed under weakly reduced pressure. The aqueous layer was washed several times with ethyl ether, and then adjusted to pH 2.5 with a 20% hydrochloric acid solution after the addition of ethyl acetate. The aqueous layer was extracted several times with ethyl acetate. The combined organic layers were washed several times with a small amount of an aqueous sodium chloride saturated solution, dried over anhydrous magnesium sulfate. The solvent was removed in vacuo to give an oily residue. The residue was dissolved in benzene and left overnight in an ice-box, yielding crystals of DL-α-hydroxy-4-(p-methoxybenzyloxycarbonyl) phenylacetic acid of 7.4 g (78.5%).

mp. 111° ~ 113° C,
IR: 1727 cm$^{-1}$.

Preparation of DL-α-Chloroacetoxy-4-(p-Methoxybenzyloxycarbonyl)phenylacetic acid 1.58 g(5 m mol) of DL-α-hydroxy-4-(p-methoxybenzyloxycarbonyl)phenylacetic acid were suspended in 10 ml of anhydrous methylene chloride and ice-cooled. To this suspension were added dropwise 5 ml of anhydrous methylene chloride solution containing 0.68 g(6 m mol) of chloroacetyl chloride with stirring over the course of 5 minutes. Then the temperature of the solution was raised slowly to ambient temperature, and the solution was stirred for 30 minutes to give a clear solution. The reaction mixture was poured into 20 ml of ice-water and adjusted to pH 2.5 with an aqueous sodium hydrogen carbonate solution. The organic layer was separated and the aqueous layer was extracted several times with methylene chloride. The combined organic layers were washed with water and dried over anhydrous magnesium sulfate. The solvent was removed in vacuo to give a pale yellow oily residue, which then was dissolved in 20 ml of benzene and left overnight in an ice-box, yielding 1.52 g (78%) of crystalline DL-α-chloroacetoxy-4-(p-methoxybenzyloxycarbonyl)phenylacetic acid of mp. 121°~125° C.

c. Preparation of 7-(DL-α-Chloroacetoxy-4-(p-Methoxybenzyloxycarbonyl)Phenylacetamido]-3-(5-Methyl-1,3,4-Thiadiazol-2-yl)Thiomethyl-3-Cephem-4-Carboxylic Acid 0.43 g(1.1 m mol) of DL-α-chloroacetoxy-4-(p-methoxybenzyloxycarbonyl)phenylacetic acid was added to 5 ml of anhydrous methylene chloride and cooled to −30° C. To the solution was added 0.11 g (1.1 m mol) of N-methylmorpholine. An anhydrous methylene chloride solution containing 0.13 g (1.2 m mol) of ethyl chloroformate was added to the above solution, stirred for an hour at −30° ~ −20° C and further for 30 minutes at −15 ~ −10° C and then cooled to −30° C. A solution of 0.35 g (1 m mol) of 7-amino-3-(5-methyl-1,3,4-thiadiazol-2-yl)thiomethyl-3-cephem-4-carboxylic acid in 0.28 ml of triethylamine and 7 ml of methanol was dropwise stirred into the above mentioned mixed anhydride solution over the course of 10 minutes and stirred for an hour at −20 ~ −10° C and further for 30 minutes at 0° C. Then the solvent was removed in vacuo and to the residue were added 10 ml of ethyl acetate and 10 ml of ice-water. 10ml of ethyl acetate were added to the residue, which then was adjusted to pH 3.3 with a 20% phosphoric acid solution, to remove insoluble materials. The aqueous solution was adjusted to pH 2.2 with phosphoric acid and saturated with sodium chloride. The ethyl acetate layer was separated and the aqueous layer was extracted several times with ethyl acetate. The combined organic layers were washed several times with an aqueous sodium chloride saturated solution and dried over anhydrous magnesium sulfate. After evaporating the solvent in vacuo, the residue was treated with ether and n-hexane, to obtain 0.55 g (77%) of 7-[DL-α-chloroacetoxy-4-(p-methoxybenzyloxycarbonyl)phenylacetamido]-3-(5-methyl-1,3,4-thiadiazol-2-yl)thiomethyl-3-cephem-4-carboxylic acid.

IR : 1780 cm$^{-1}$, UV λmax : 270 n.m (95% ethanol).

TLC : RF = 0.50 (acetonitrile : water = 4 : 1, iodo azide was used as a coloring agent).

d. Preparation of 7-[DL-α-Hydroxy-4-(P-Methoxybenzyloxycarbonyl)-Phenylacetamido]-3-(5-Methyl-1,3,4-Thiadiazol-2-YL)Thiomethyl-3-Cephem-4-Carboxylic Acid 0.55 g (0.76 m mol) of 7-[DL-α-chloroacetoxy-4-(p-methoxybenzyloxycarbonyl)phenylacetamido]-3-(5-methyl-1,3,4-thiadiazol-2-yl)thiomethyl-3-cephem-4-carboxylic acid and 0.066 g (0.9 m mol) of thiourea were added to 10 ml of phosphate buffer (0.2 mol, pH 6.3). The mixture was adjusted to pH 6.5 with a sodium hydrogen carbonate solution and stirred at 45° C for 15 hours. The reaction mixture was cooled in an ice-water bath, adjusted to pH 9.0 with sodium carbonate solution, washed with ether and then treated with activated carbon. 10 ml of ethyl acetate were added to the aqueous solution, followed by adjustment to pH 2.5 with 20% phosphoric acid solution. The solution was saturated with sodium chloride. After separating the ethyl acetate layer, the aqueous layer was extracted several times with ethyl acetate.

The combined organic layers were washed with an aqueous sodium chloride saturated solution, dried over anhydrous magnesium sulfate and evaporated in vacuo.

The residue was treated with ethyl ether and n-hexane to give a fine powder of 0.41 g (83 %) of 7-[DL-α-hydroxy-4-(p-methoxybenzyloxycarbonyl)-phenylacetamido]-3-(5-methyl-1,3,4-thiadiazol-2-yl)thiomethyl-3-cephem-4-carboxylic acid.

IR : 1780 cm$^{-1}$ UV λmax : 270 n.m. (95% ethanol).

Then, the above product was converted into the corresponding 7-(DL-α-hydroxy-4-carboxyphenylacetamido)-3-(5-methyl-1,3,4-thiadiazol-2-yl)thiomethyl-3-cephem-4-carboxylic acid of mp 95° ~ 102° C, by treatment with trifluoroacetic acid in anisole and benzene.

EXAMPLES 4 – 10

A. Instead of DL-α-chloroacetoxy-4-(p-methoxybenzyloxycarbonyl)phenylacetic acid and 7-amino-3-(5-methyl-1,3,4-thiadiazol-2-yl)thiomethyl-3-cephem-4-carboxylic acid used in (c) of Example 3, each of 4. DL-α-chloroacetoxy-4-ethoxycarbonylphenylacetic acid (mp 100° ~ 103° C) and 7-amino-3-(5-methyl-1,3,4-thiadiazol-2-yl)thiomethyl-3-cephem-4-carboxylic acid;
5. DL-α-chloroacetoxy-4-ethoxycarbonylphenylacetic acid (mp 100° ~ 103° C) and 7-amino-3-(1,3,4-thiadiazol-2-yl)thiomethyl-3-cephem-4-carboxylic acid;
6. DL-α-chloroacetoxy-4-ethoxycarbonylphenylacetic acid and 7-amino-3-(1-methyl-1H-1,2,3,4-tetrazol-5-yl)thiomethyl-3-cephem-4-carboxylic acid;
7. DL-α-chloroacetoxy-4-ethoxycarbonylphenylacetic acid and 7-amino-3-acetoxymethyl-3-cephem-4-carboxylic acid;
8. DL-α-chloroacetoxy-4-ethoxycarbonylphenylacetic acid and 7-amino-3-azidomethyl-3-cephem-4-carboxylic acid,
9. DL-α-chloroacetoxy-4-(2-methylpropoxycarbonyl)phenylacetic acid (mp 96° ~ 98° C) and 7-amino-3-(5-methyl-1,3,4-thiadiazol-2-yl)thiomethyl-3-cephem-4-carboxylic acid;
10. DL-α-chloroacetoxy-4-(p-nitrobenzyloxycarbonyl)phenylacetic acid (mp 114° ~ 117° C) and 7-amino-3-(5-methyl-1,3,4-thiadiazol-2-yl)thiomethyl-3-cephem-4-carboxylic acid was used and treated in accordance with (c) of Example 3.

The respective products were as follows.

4. 7-(DL-α-chloroacetoxy-4-ethoxycarbonylphenylacetamido)-3-(5-methyl-1,3,4-thiadiazol-2-yl)thiomethyl-3-cephem-4-carboxylic acid:
mp 122° ~ 133° C (decomp).
IR : 1775, 1720, 1700 cm⁻¹.
UV λmax : 240, 273 n.m.
Yield : 74%.

5. 7-(DL-α-chloroacetoxy-4-ethoxycarbonylphenylacetamido)-3-(1,3,4-thiadiazol-2-yl)thiomethyl-3-cephem-4-carboxylic acid:
Yield : 74%.
IR : 1780 cm⁻¹
UV λmax : 273 n.m.

6. 7-(DL-α-chloroacetoxy-4-ethoxycarbonylphenylacetamido)-3-(1-methyl-1H-1,2,3,4-tetrazol-5-yl)thiomethyl-3-cephem-4-carboxylic acid;
Yield : 72%.
IR : 1775 cm⁻¹
UV λmax : 274 n.m.

7. 7-(DL-α-chloroacetoxy-4-ethoxycarbonylphenylacetamido)-3-acetoxymethyl-3-cephem-4-carboxylic acid:
Yield : 71%.
IR : 1775 cm⁻¹,
UV λmax : 263 n.m.

8. 7-(DL-α-chloroacetoxy-4-ethoxycarbonylphenylacetamido)-3-azidomethyl-3-cephem-4-carboxylic acid;
Yield : 78% IR : 2100, 1770 cm⁻¹
UV λmax : 263 n.m.

9. 7-[DL-α-chloroacetoxy-4-(2-methylpropoxycarbonyl)phenylacetamido]-3-(5-methyl-1,3,4-thiadiazol-2-yl)thiomethyl-3-cephem-4-carboxylic acid;
Yield : 76%.
IR : 1780 cm⁻¹.
UV λmax : 273 n.m.

10. 7-[DL-α-chloroacetoxy-4-(p-nitrobenzyloxycarbonyl)phenylacetamido]-3-(5-methyl-1,3,4-thiadiazol-2-yl)thiomethyl-3-cephem-4-carboxylic acid;
Yield : 76%.
IR : 1775, 1720, 1700 cm⁻¹
UV λmax : 273 n.m.

B. Instead of 7-[DL-α-chloroacetoxy-4-(p-methoxybenzyloxycarbonyl)phenylacetamido]-3-(5-methyl-1,3,4-thiadiazol-2-yl)thiomethyl-3-cephem-4-carboxylic acid used in (d) of Example 3, each of 4. 7-(DL-α-chloroacetoxy-4-ethoxycarbonylphenylacetamido)-3-(5-methyl-1,3,4-thiadiazol-2-yl)thiomethyl-3-cephem-4-carboxylic acid;
5. 7-(DL-α-chloroacetoxy-4-ethoxycarbonylphenylacetamido)-3-(1,3,4-thiadiazol-2-yl)thiomethyl-3-cephem-4-carboxylic acid;
6. 7-(DL-α-chloroacetoxy-4-ethoxycarbonylphenylacetamido)-3-(1-methyl-1H-1,2,3,4-tetrazol-5-yl)thiomethyl-3-cephem-4-carboxylic acid;
7. 7-(DL-α-chloroacetoxy-4-ethoxycarbonylphenylacetamido)-3-acetoxymethyl-3-cephem-4-carboxylic acid;
8. 7-(DL-α-chloroacetoxy-4-ethoxycarbonylphenylacetamido)-3-azidomethyl-3-cephem-4-carboxylic acid;
9. 7-[DL-α-chloroacetoxy-4(2-methylpropoxycarbonyl)phenylacetamido]-3-(5-methyl-1,3,4-thiadiazol-2-yl)thiomethyl-3-cephem-4-carboxylic acid;
10. 7-[DL-α-chloroacetoxy-4-(p-nitrobenzyloxycarbonyl)phenylacetamido]-3-(5-methyl-1,3,4-thiadiazol-2-yl)thiomethyl-3-cephem-4-carboxylic acid, was used and treated in accordance with (d) of Example 3.

The respective products were as follows:

4. 7-(DL-α-hydroxy-4-ethoxycarbonylphenylacetamido)-3-(5-methyl-1,3,4-thiadiazol-2-yl)thiomethyl-3-cephem-4-carboxylic acid; mp. about 112° C(decomp.).
Yield : 84%.
IR : 1775, 1720, 1700 cm⁻¹.
UV λmax : 243, 272 n.m.
MIC : 25γ/ml. against E. coli.

5. 7-(DL-α-hydroxy-4-ethoxycarbonylphenylacetamido)-3-(1,3,4-thiadiazol-2yl)thiomethyl-3-cephem-4-carboxylic acid;
Yield : 87%.
IR: 1775, 1720, 1700 cm⁻¹.
UV λmax : 242, 272 n.m.
MIC: E. Coli, 25γ/ml.

6. 7-(DL-α-hydroxy-4-ethoxycarbonylphenylacetamido)-3-(1-methyl-1H-1,2,3,4-tetrazol-5-yl)thiomethyl-3-cephem-4-carboxylic acid;
Yield : 86%.
IR : 1780 cm⁻¹.
UV λmax : 274 n.m.
MIC : E. coli, 3 γ/ml.

7. 7-(DL-α-hydroxy-4-ethoxycarbonylphenylacetamido)-3-acetoxymethyl-3-cephem-4-carboxylic acid;
Yield : 80%.
IR : 1775 cm⁻¹.
UV λmax : 262 n.m.

MIC : E.coli, 6γ/ml.

8. 7-(DL-α-hydroxy-4-ethoxycarbonyl-phenylacetamido)-3-azidomethyl-3-cephem-4-carboxylic acid;
Yield : 57%.
IR :1775, 2100 cm⁻¹.
UV λmax : 263 n. m.

9. 7-(DL-α-hydroxy-4-(2-methylpropoxycarbonyl)-phenylacetamido)-3-)5-methyl-1,3,4-thiadiazol-2-yl)thiomethyl-3-cephem-4-carboxylic acid;
Yield : 84%.
IR : 1780 cm⁻¹.
UV λmax : 272 n.m.
MIC : E. coli, 3γ/ml.

10. 7-[DL-α-hydroxy-4-(p-nitrobenzyloxycarbonyl)-phenylacetamido]-3-(5-methyl-1,3,4-thiadiazol-2-yl)thiomethyl-3-cephem-4-carboxylic acid;
Yield : 82%.
IR : 1775, 1720, 1700 cm⁻¹.
UVλmax : 272 n.m.
MIC : E.coli, 6γ/ml.

EXAMPLE 11 a. Preparation of 7-(DL-α-Chloroacetoxy-4-Carboxyphenylacetamido)-3-(5-Methyl-1,3,4-Thiadiazol-2-yl)Thiomethyl-3-Cephem-4-Carboxylic Acid A solution of 3 m mol of DL-α-chloroacetoxy-4-carboxyphenylacetic acid and 5 m mol of N-methylmorpholine in 20 ml of anhydrous tetrahydrofuran was cooled to −20° C. To the solution were dropwise added 3 ml of ethyl chloroformate, followed by stirring for 2 hours at −20° ∼ −10° C and cooled to −30° C.

On the other hand, a mixture of 3 m mol of 7-amino-3-(5-methyl-1,3,4-thiadiazol-2-yl)thiomethyl-3-cephem-4-carboxylic acid, 4.5 m mol of hexamethyldisilazane and 10 ml of methylene chloride was heated for 30 minutes and condensed under reduced pressure. The residue was dissolved in 10 ml of methylene chloride.

This solution was added dropwise to the above tetrahydrofuran solution at −30° C over the course of 30 minutes, for followed by stirring for an hour at −30° ∼ −10° C and further 1.5 hours at −10° ∼ 0° C. The solvent was distilled off in vacuo. Ice-water was added to the residue, adjusting to pH 2 with a 20% hydrochloric acid solution. The precipitated product was collected, dried and purified by silica gel column chromatography eluting with benzene/ethyl acetate.
7-(DL-α-Chloroacetoxy-4-carboxy phenylacetamido)-3-(5-methyl-1,3,4-thiadiazol-2-yl)thiomethyl-3-cephem-4-carboxylic acid was thus obtained in a yield of 37%.
IR : 1775 cm⁻¹ (β-lactam).
UV λmax : 274 n.m. (ethanol).

This product was treated with thiourea in a phosphate buffer (pH 6.7) at 45° C, to obtain 7-(DL-α-hydroxy-4-carboxyphenylacetamido)-3-(5-methyl-1,3,4-thiadiazol-2-yl)thiomethyl-3-cephem-4-carboxylic acid.
mp 95° ∼ 102° C (decomp)
IR : 1775 cm⁻¹ (β-lactam).
UV λmax : 273 n.m. (ethanol).
MIC : E.Coli, 0.8γ/ml Proteus vulgaris 1.6γ/ml

EXAMPLES 12 ∼ 13

Instead of 7-amino-3-(5-methyl-1,3,4-thiadiazol-2-yl)thiomethyl-3-cephem-4-carboxylic acid used in Example 11, each of
12. 7-amino-3-(1,3,4-thiadiazol-2-yl)thiomethyl-3-cephem-4carboxylic acid,
13. 7-amino-3-(1-methyl-1H-1,2,3,4-tetrazol-5-yl)thiomethyl-3-cephem-4-carboxylic acid,
was used and treated as described in Example 11. The respective products were as follows.
12. 7-(DL-α-hydroxy-4-carboxyphenylacetamido)-3-(1,3,4-thiadiazol-2-yl)thiomethyl-3-cephem-4-carboxylic acid,
IR : 1775 cm⁻¹.
UV λmax : 274 n.m.
MIC : E. Coli, 0.8γ/ml. P. vulgaris, 1.60γ/ml
13. 7-(DL-α-hydroxy-4-carboxyphenylacetamido)-3-(1-methyl-1H-1,2,3,4-tetrazol-5-yl)thiomethyl-3-cephem-4-carboxylic acid
IR : 1770 cm⁻¹.
UV λmax : 274 n.m.
MIC: E. Coli, 0.8 γ/ml P. vulgaris, 0.8 γ/ml

What I claim is:
1. A compound of the formula

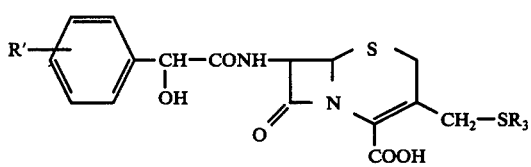

wherein R' is carboxy, p-methoxy-benzyloxycarbonyl, ethoxycarbonyl, 2-methyl-propoxycarbonyl, p-nitrobenzyloxy-carbonyl 2,2,2-trichloroethoxycarbonyl, phenacyloxycarbonyl, diacetylmethoxycarbonyl, 1-methoxycarbonyl-2oxopropan-1-yl-oxycarbonyl, and 1-ethoxycarbonyl-2-oxopropan-1-yl-oxycarbonyl, and
$R_3$ is a heterocycle selected from the group consisting of the thiadiazolyl, tetrazolyl, triazolyl, oxadiazolyl, oxopyridinyl, imidazolyl and pyrimidinyl groups, and the corresponding methyl-substituted thiadiazolyl, tetrazolyl, triazolyl, oxadiazolyl, oxopyridinyl, imidazolyl and pyrimidinyl groups,
and pharmaceutically acceptable non-toxic salts thereof.

2. 7-[α-hydroxy-4(p-methoxybenzyloxycarbonyl)-phenylacetamido]-3-(5-methyl-1,3,4-thiadiazol-2-yl)thiomethyl-3-cephem-4-carboxylic acid according to claim 1.
3. 7-(α-hydroxy-4-ethoxycarbonylphenylacetamido)-3-(5-methyl-1,3,4-thiadiazol-2-yl)thiomethyl-3-cephem-4carboxylic acid according to claim 1.
4. 7-(α-hydroxy-4-ethoxycarbonylphenylacetamido)-3-(1,3,4-thiadiazol-2-yl)thiomethyl-3-cephem-4-carboxylic acid according to claim 1.
5. 7-(α-hydroxy-4-ethoxycarbonylphenylacetamido)-3-(1-methyl-1H-1,2,3,4-tetrazol-5-yl)thiomethyl-3-cephem-4-carboxylic acid according to claim 1.
6. 7-[α-hydroxy-4-(2-methylpropoxycarbonyl)-phenylacetamido]-3-(5-methyl-1,3,4-thiadiazol-2-yl)thiomethyl-3-cephem-4-carboxylic acid according to claim 1.
7. 7-[α-hydroxy-4-(p-nitrobenzyloxycarbonyl)-phenylacetamido]-3-(5-methyl-1,3,4-thiadiazol-2-yl)thiomethyl-3-cephem-4-carboxylic acid according to claim 1.
8. 7-(α-hydroxy-4-carboxyphenylacetamido)-3-(5-methyl-1,3,4-thiadiazol-2-yl)thiomethyl-3-cephem-4-carboxylic acid.

* * * * *

UNITED STATES PATENT OFFICE
CERTIFICATE OF CORRECTION

Patent No. 4,064,122    Dated December 20, 1977

Inventor(s) Toshiyasu Ishimaru

It is certified that error appears in the above-identified patent and that said Letters Patent are hereby corrected as shown below:

Title page, formula in the Abstract:

" 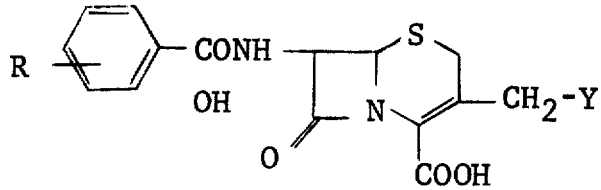 " should read

-- 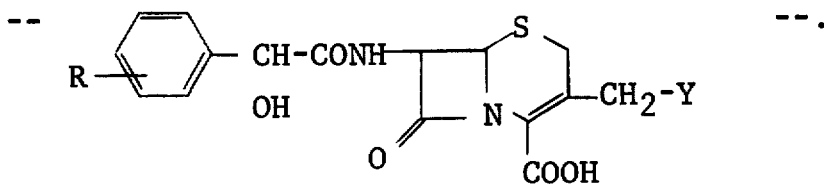 --.

Column 3, line 32: "chloro." should read -- chloroformate. --; line 66: "0°C, although" should read -- 0°C, is sufficient, although --.

Column 4, line 15: "some" should read -- same --.

Column 6, lines 4-5: "33. 7-[-hydroxy-4(or 3)-(p-nitrobenzyloxycarbonyl)-phenylacetamido]cephalosporanic acid," should read -- 33. 7-[α-hydroxy-4(or 3)-(p-nitrobenzyloxycarbonyl)phenylacetamido]cephalosporanic acid, --; line 12: "obtained object compounds" should read -- obtained compounds --; line 27: "7-acryl" should read -- 7-acyl --.

UNITED STATES PATENT OFFICE
CERTIFICATE OF CORRECTION

Patent No. 4,064,122                     Dated December 20, 1977

Inventor(s) Toshiyasu Ishimaru

It is certified that error appears in the above-identified patent and that said Letters Patent are hereby corrected as shown below:

Column 8, lines 45-46: "7-(D-α-chloroacetoxy-phenylacetamido)-cephalospornaic" should read -- 7-(D-α-chloroacetoxy-phenylacetamido)-cephalosporanic --.

Column 9, line 47: "solution," should read -- solution. --.

Column 13, lines 9-11: "9. 7-(DL-α-hydroxy-4-(2-methylpropoxy-carbonyl)-phenylacetamido)-3-)5-methyl-1,3,4-thiadiazol-2-yl)thiomethyl-3-cephem-4-carboxylic acid;" should read -- 9. 7-(DL-α-hydroxy-4-(2-methylpropoxy-carbonyl)-phenylacetamido)-3-(5-methyl-1,3,4-thiadiazol-2-yl)thiomethyl-3-cephem-4-carboxylic acid; --.

Column 14, claim 3: "...3-(5-methyl-1,3,4-thiadizol-2-yl)thio-methyl-3-cephem-4carboxylic acid" should read -- ...3-(5-methyl-1,3,4-thiadiazol-2-yl)thiomethyl-3-cephem-4-carboxylic acid --.

Signed and Sealed this

Eleventh Day of April 1978

[SEAL]

Attest:

RUTH C. MASON
Attesting Officer

LUTRELLE F. PARKER
Acting Commissioner of Patents and Trademarks